United States Patent [19]

Wallace et al.

[11] Patent Number: 5,554,749

[45] Date of Patent: Sep. 10, 1996

[54] FUNCTIONALIZED MACROCYCLIC LIGANDS FOR IMAGING APPLICATIONS

[75] Inventors: Rebacca A. Wallace, Manchester; Dennis A. Moore, Ferguson, both of Mo.

[73] Assignee: Mallinckrodt Medical, Inc.

[21] Appl. No.: 182,251

[22] Filed: Jan. 14, 1994

[51] Int. Cl.$^6$ ............................. C07D 255/02; C07F 5/00
[52] U.S. Cl. ...................... 540/474; 540/450; 540/452; 540/470; 534/10; 534/14; 534/15; 424/9.3
[58] Field of Search ..................... 540/450, 452, 540/470, 474; 534/10, 14, 15; 424/9.3

[56] References Cited

U.S. PATENT DOCUMENTS

| | | | |
|---|---|---|---|
| 5,247,075 | 9/1993 | Parker et al. | 540/474 |
| 5,284,944 | 2/1994 | Madison et al. | 540/474 |
| 5,342,606 | 8/1994 | Sherry et al. | 540/474 |

*Primary Examiner*—Mukund J. Shah
*Assistant Examiner*—Pavanaram K. Sripada
*Attorney, Agent, or Firm*—Brian K. Stierwalt

[57] ABSTRACT

The present invention provides new and structurally diverse compositions comprising compounds of the general formula:

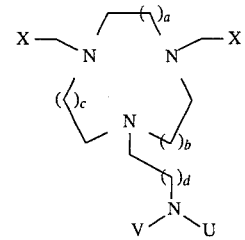

Wherein U is $-(CH_2)_nX$ or $-(CH_2)_nNR_1(CH_2)X$; $R_1$ is hydrogen, $C_1-C_8$ alkyl, $C_1-C_8$ hydroxyalkyl or $C_1-C_8$ alkoxyalkyl; V is $-(CH_2)_nX$, $-(CH_2)_nNR_1(CH_2)X$, hydrogen, $C_1-C_8$ alkyl, $C_1-C_8$ hydroxyalkyl or $C_1-C_8$ alkoxyalkyl; V and $R_1$ may jointly be $-(CH_2)_m-$ to form a heterocyclic ring; X is $-CO_2H$, $-PO_3H_2$, $-SO_3H$ or $-CONHOH$; a, b, c, d, n and m may be the same or different and are from one to about ten, preferably from one to about three.

Methods for imaging using compositions of the invention are also provided.

21 Claims, No Drawings

FUNCTIONALIZED MACROCYCLIC LIGANDS FOR IMAGING APPLICATIONS

FIELD OF THE INVENTION

This invention relates to magnetic resonance imaging (MRI), x-ray imaging, and radiopharmaceuticals. More particularly the invention relates to methods and compositions for enhancing MRI, x-ray imaging, and radiopharmaceuticals.

BACKGROUND OF THE INVENTION

The use of contrast agents in diagnostic medicine is rapidly growing. In X-ray diagnostics, for example, increased contrast of internal organs, such as the kidneys, the urinary tract, the digestive tract, the vascular system of the heart (angiography), and so forth is obtained by administering a contrast agent which is substantially radiopaque. In conventional proton MRI diagnostics, increased contrast of internal organs and tissues may be obtained by administering compositions containing paramagnetic metal species which increase the relaxivity of surrounding protons. In ultrasound diagnostics, improved contrast is obtained by administering compositions having acoustic impedances different than that of blood and other tissues.

The recently developed technique of MRI encompasses the detection of certain atomic nuclei utilizing magnetic fields and radio-frequency radiation. It is similar in some respects to X-ray computed tomography (CT) in providing a cross-sectional display of the body organ anatomy with excellent resolution of soft tissue detail. As currently used, the images produced constitute a map of the proton density distribution, the relaxation times, or both, in organs and tissues. The technique of MRI is advantageously non-invasive as it avoids the use of ionizing radiation.

While the phenomenon of NMR was discovered in 1945, it is only recently that it has found application as a means of mapping the internal structure of the body as a result of the original suggestion of Lauterbur (*Nature*, 242, 190–191 [1973]). The fundamental lack of any known hazard associated with the level of the magnetic and radio-frequency fields that are employed renders it possible to make repeated scans on vulnerable individuals. In addition to standard scan planes (axial, coronal, and sagittal), oblique scan planes can also be selected.

With an MRI experiment, the nuclei under study in a sample (e.g. protons) are irradiated with the appropriate radio-frequency (RF) energy in a highly uniform magnetic field. These nuclei, as they relax, subsequently emit RF at a sharp resonance frequency. The resonance frequency of the nuclei depends on the applied magnetic field.

According to known principles, nuclei with appropriate spin, when placed in an applied magnetic field (B, expressed generally in units of gauss or Tesla [$10^4$ gauss]) align in the direction of the field. In the case of protons, these nuclei precess at a frequency, f, of 42.6 MHz, at a field strength of 1 Tesla. At this frequency, an RF pulse of radiation will excite the nuclei and can be considered to tip the net magnetization out of the field direction, the extent of this rotation being determined by the pulse duration and energy. After the RF pulse, the nuclei "relax" or return to equilibrium with the magnetic field, emitting radiation at the resonant frequency. The decay of the emitted radiation is characterized by two relaxation times, i.e., $T_1$, the spin-lattice relaxation time or longitudinal relaxation time, that is, the time taken by the nuclei to return to equilibrium along the direction of the externally applied magnetic field, and $T_2$, the spin-spin relaxation time associated with the dephasing of the initially coherent precession of individual proton spins. These relaxation times have been established for various fluids, organs and tissues in different species of mammals.

In MRI, scanning planes and slice thicknesses can be selected. This selection permits high quality transverse, coronal and sagittal images to be obtained directly. The absence of any moving parts in MRI equipment promotes high reliability. It is believed that MRI has a greater potential than CT for the selective examination of tissue characteristics in view of the fact that in CT, X-ray attenuation coefficients alone determine image contrast, whereas at least five separate variables ($T_1$, $T_2$, proton density, pulse sequence and flow) may contribute to the MRI signal.

By reason of its sensitivity to subtle physicochemical differences between organs and/or tissues, it is believed that MRI may be capable of differentiating different tissue types and in detecting diseases which induce physicochemical changes that may not be detected by X-ray or CT which are only sensitive to differences in the electron density of tissue.

As noted above, two of the principal imaging parameters are the relaxation times, $T_1$ and $T_2$. For protons (or other appropriate nuclei), these relaxation times are influenced by the environment of the nuclei, (e.g., viscosity, temperature, and the like). These two relaxation phenomena are essentially mechanisms whereby the initially imparted radio-frequency energy is dissipated to the surrounding environment. The rate of this energy loss or relaxation can be influenced by certain other nuclei which are paramagnetic. Chemical compounds incorporating these paramagnetic nuclei may substantially alter the $T_1$ and $T_2$ values for nearby protons. The extent of the paramagnetic effect of a given chemical compound is a function of the environment.

In general, paramagnetic species such as ions of elements with atomic numbers of 21 to 29, 42 to 44 and 58 to 70 have been found effective as MRI image contrasting agents. Examples of suitable ions include chromium(III), manganese(II), manganese(III), iron(II), iron(III), cobalt(II), nickel(II), copper(II), praseodymium(III), neodymium(III), samarium(III), and ytterbium(III). Because of their very strong magnetic moments, gadolinium(III), terbium(III), dysprosium(III), holmium(III) and erbium(III) are preferred. Gadolinium(III) ions have been particularly preferred as MRI contrasting agents.

Typically, paramagnetic ions have been administered in the form of complexes with organic complexing agents. Such complexes provide the paramagnetic ions in a soluble, non-toxic form, and facilitate their rapid clearence from the body following the imaging procedure. Gries et al., U.S. Pat. No. 4,647,447, disclose complexes of various paramagnetic ions with conventional aminocarboxylic acid complexing agents. A preferred complex disclosed by Gries et al. is the complex of gadolinium(III) with diethylenetriamine-pentaacetic acid ("DTPA").

Paramagnetic ions, such as gadolinium(III), have been found to form strong complexes with DTPA, ethylenediamine-tetraacetic acid ("EDTA"), and with tetraazacyclododecane-N,N',N",N"'-tetraacetic acid ("DOTA").

These complexes do not dissociate substantially in physiological aqueous fluids. The gadolinium complex of DTPA has a net charge of −2, whereas the gadolinium complex of EDTA or DOTA has a net charge of −1, and both are generally administered as soluble salts. Typical salts are sodium and N-methylglucamine. The administration of salts is attended by certain disadvantages. These salts can raise the in vivo ion concentration and cause localized disturbances in osmolality, which in turn, can lead to edema and other undesirable reactions.

Efforts have been made to design new ionic and neutral paramagnetic metal complexes which avoid or minimize the above mentioned disadvantages. In general, this goal can be achieved by converting one or more of the free carboxylic acid groups of the complexing agent to neutral, non-ionizable groups. For example, S. C. Quay, in U.S. Pat. Nos. 4,687,658 and 4,687,659, discloses alkylester and alkylamide derivatives, respectively, of DTPA complexes. Similarly, published Dean et al., U.S. Pat. No. 4,826,673 discloses mono- and polyhydroxyalkylamide derivatives of DTPA and their use as complexing agents for paramagnetic ions. It can also be achieved by covalent attachment of organic cations to the complexing agent in such a manner that the sum of positive and negative charges in the resulting metal complex is zero.

The nature of additional substituents in the complexing agent can have a significant impact on tissue specificity. Hydrophilic complexes tend to concentrate in the interstitial fluids, whereas lipophilic complexes tend to associate with cells. Thus, differences in hydrophilicity can lead to different applications of the compounds. See, for example, Weinmann et al., *AJR*, 142, 679 (March 1984) and Brasch, et al., *AJR*, 142, 625 (March 1984).

Finally, toxicity of paramagnetic metal complexes is greatly affected by the nature of the complexing agents. In vivo release of free metal ions from the complex is a major cause of toxicity. Four principal factors are important in the design of chelates for making paramagnetic metal complexes that are highly stable in vivo and less toxic. The first three factors are thermodynamic in nature whereas the fourth involves chelate kinetics. The first factor is the thermodynamic stability constant of the metal-ligand. The thermodynamic stability constant indicates the affinity that the totally unprotonated ligand has for a metal. The second factor is the conditional stability constant which takes into account the pH and is important when considering stability under physiological pH. The selectivity of the ligand for the paramagnetic metal over other endogenous metal ions such as zinc, iron, magnesium and calcium is the third factor. In addition to the three thermodynamic considerations, complexes with structural features that make in vivo transmetallation reactions much slower than their clearance rates would be predicted to have low toxicities. Therefore, in vivo reaction kinetics are a major factor in the design of stable complexes. See, for example, Cacheris et al., *Magnetic Resonance Imaging*, 8:467 (1990) and Oksendal, et al., *JMRI*, 3:157 (1993).

A need continues to exist for new and structurally diverse compounds for use as imaging agents and radiopharmaceuticals. There is a further need to develop highly stable complexes with good relaxivity and osmolar characteristics.

SUMMARY OF THE INVENTION

The present invention provides new and structurally diverse compositions comprising compounds of the general formula:

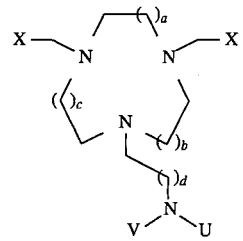

Wherein U is $-(CH_2)_nX$ or $-(CH_2)_nNR_1(CH_2)X$; $R_1$ is hydrogen, $C_1-C_8$ alkyl, $C_1-C_8$ hydroxyalkyl or $C_1-C_8$ alkoxyalkyl; V is $-(CH_2)_nX$, $-(CH_2)_nNR_1(CH_2)X$, hydrogen, $C_1-C_8$ alkyl, $C_1-C_8$ hydroxyalkyl or $C_1-C_8$ alkoxyalkyl; V and $R_1$ may jointly be $-(CH_2)_m-$ to form a heterocyclic ring; X is $-CO_2H$, $-PO_3H_2$, $-SO_3H$ or $-CONHOH$; a, b, c, d, n and m may be the same or different and are from one to about ten, preferably from one to about three.

Also provided are compositions comprising complexes of the compounds with metal ions of the general formula

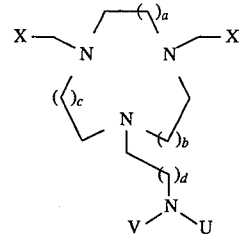

Wherein U is $-(CH_2)_nY$ or $-(CH_2)_nNR_1(CH_2)Y$; $R_1$ is hydrogen, $C_1-C_8$ alkyl, $C_1-C_8$ hydroxyalkyl or $C_1-C_8$ alkoxyalkyl; V is $-(CH_2)_nY$ or $-(CH_2)_nNR_1(CH_2)Y$, hydrogen, $C_1-C_8$ alkyl, $C_1-C_8$ hydroxyalkyl or $C_1-C_8$ alkoxyalkyl; optionally V and $R_1$ may jointly be $-(CH_2)_m-$ to form a heterocyclic ring; Y is $-CO_2M$, $-PO_3HM$, $-SO_3M$ or $-CONHOM$; a, b, c, d, n and m may be the same or different and are from one to about ten, preferably from one to about three; M is a metal ion equivalent and/or a physiologically acceptable cation of an organic base.

Compositions comprising the above formulas wherein M is a radioactive metal ion, a paramagnetic ion, or a metal ion capable of absorbing x-rays are also provided for use as radiopharmaceuticals, magnetic resonance imaging, and x-ray contrast agents, respectively.

Diagnostic compositions comprising the compounds of the invention are also provided. Methods of performing diagnostic procedures with compositions of the invention are also disclosed. The methods comprise administering to a patient an effective amount of the compositions of the invention and optionally subjecting the patient to an imaging procedure of imaging.

DETAILED DESCRIPTION

The compositions of the invention are suitable for use with a variety of modalities including x-rays, magnetic resonance imaging and radiopharmaceuticals.

The functionality of the R groups of the compositions of the invention afford the additional capability of derivatization to biomolecules and synthetic polymers. Biomolecule refers to all natural and synthetic molecules that play a role in biological systems. Biomolecules include hormones, amino acids, peptides, peptidomimetics, proteins, deoxyribonucleic acid (DNA) ribonucleic acid (RNA), lipids, albumins, polyclonal antibodies, receptor molecules, receptor binding molecules, monoclonal antibodies and aptamers. Specific examples of biomolecules include insulins, prostaglandins, growth factors, liposomes and nucleic acid probes. Examples of synthetic polymers include polylysine, arborols, dendrimers, and cyclodextrins. The advantages of using biomolecules include enhanced tissue targeting through specificity and delivery. Coupling of the chelating moieties to biomolecules can be accomplished by several known methods (e.g., Krejcarek and Tucker *Biochem. Biophys. Res. Comm*, 30, 581 (1977); Hnatowich, et al. *Science*, 220, 613 (1983). For example, a reactive moiety present in one of the R groups is coupled with a second reactive group located on the biomolecule. Typically, a nucleophilic group is reacted with an electrophilic group to form a covalent bond between the biomolecule and the chelate. Examples of nucleophilic groups include amines, anilines, alcohols, phenols, thiols and hydrazines. Electrophilic group examples include halides, disulfides, epoxides, maleimides, acid chlorides, anhydrides, mixed anhydrides, activated esters, imidates, isocyanates and isothiocyanates. And finally, the compositions of the invention should provide the additional advantage of being kinetically inert.

Examples of suitable alkyl groups for use with the invention include methyl, ethyl, propyl, isopropyl, butyl, cyclohexyl, heptyl and octyl. Suitable alkoxy groups include methoxy, ethoxy, propoxy, butoxy, pentoxy, hexoxy, heptoxy and octoxy. Hydroxyalkyl groups suitable for use with the invention include both mono and poly hydroxyalkyls such as hydroxyethyl, 2-hydroxypropyl, 2,3-dihydroxypropyl, 2,3,4-trihydroxybutyl, tris(hydroxymethyl)methyl and 2-hydroxy-1 -hydroxymethyl-ethyl. Suitable alkoxyalkyl groups include methoxymethyl, 2,3-dimethoxypropyl, tris-(methoxymethyl)methyl, and 2-methoxy-1-methoxymethylethyl.

Examples of suitable compounds of the invention are 1-[3 -[N-(2,3-dihydroxypropyl)-N-(carboxymethyl)-amino]propyl]-4,7 -bis-(carboxymethyl)-1,4,7-triazacyclononane; 1-[2-(4 -carboxymethyl-piperazino)ethyl]-4,7-bis-(carboxymethyl)-1,4,7-triazacyclononane; 1-[2[N-(2-hydroxyethyl)-N-(phosphonomethyl)-amino]ethyl]-4,7-bis(phosphonomethyl)-1,4,7-triazacyclononane; and 1-[$N^3,N^6$-bis [(2-hydroxyethyl)]-$N^6$ -(sulfonomethyl)-3,6-diaza]hexyl-4, 7-bis-(sulfonomethyl)-1,4,7-triazacyclononane.

Complexes of the novel ligands or compounds of the invention with one or more central metal ions or metal ion equivalents such as paramagnetic metals praseodymium(III), neodymium(III), samarium(III), ytterbium(III) terbium(III), dysprosium(III), holmium(III), erbium(III), iron(II), iron(III), manganese(II), manganese(III), gadolinium(III), chromium(III), cobalt(II) and nickel(II) are useful for enhancing magnetic resonance images. While such metal ions are themselves paramagnetic in nature and capable of altering the magnetic resonance signal characteristics of body tissues, organs or fluids, they may exhibit significant toxicity when administered in the form of ionic salts. However, novel complexes of the invention are relatively or substantially nontoxic and therefore useful for enhancing magnetic resonance images by favorably altering relaxation times $T_1$ and $T_2$ and affording improved contrast between normal and diseased tissues or organs.

The preferred complexes of the invention are those formed from the above ligands and iron(II), iron(III), manganese(II), manganese(III) and gadolinium(III) as the central metal ion or ions. Depending upon the particular ligand employed and the particular central metal ion used, the complexes formed may be neutral, ionic, cationic, or zwitterionic in nature, or they may be negatively charged. The neutral complexes are generally preferred and generally appear to exhibit relatively lower toxicity as compared to ionic or negatively charged complexes. The negatively charged complexes formed by the ligands and central metal ions enumerated above may be further complexed with one or more cations of an inorganic or organic base which are physiologically tolerated. Examples of cations for further complexing include sodium, potassium, calcium, and salts of N-methylglucamine, and diethanolamine.

Examples of preferred compounds of the invention and one or more central metal ions (i.e., complexes) include 1-[3-[N-( 2,3-dihydroxypropyl)-N-(carboxymethyl)-amino] propyl]-4,7-bis-(carboxymethyl)- 1,4,7-triazacyclononane, gadolinium(III) complex; 1-[2-(4-carboxymethyl)piperazino)ethyl]-4,7-bis-(carboxymethyl)- 1,4,7-triazacyclononane, gadolinium(III) complex; 1-[2-[N-(2-hydroxyethyl)-N-(phosphonomethyl)-amino]ethyl]-4,7-bis(phosphonomethyl)-1,4,7-triazacyclononane, iron(III) complex; 1-[2-[N-(2-hydroxyethyl)-N-(phosphonomethyl)-amino]ethyl]-4,7-bis(phosphonomethyl)-1,4,7 -triazacyclononane, gadolinium(III) complex; and 1-[$N^5,N^6$-bis-[(2-hydroxyethyl]-$N^6$-[(sulfonomethyl)]-3,6-diaza]hexyl-4,7 -bis-(sulfonomethyl)-1,4,7-triazacyclononane, gadolinium(III) complex.

In addition to their utility in magnetic resonance imaging procedures, the compositions of the invention can also be employed for delivery of either radiopharmaceuticals or heavy metals for x-ray contrast into the body. For use in diagnostic and therapeutic radiopharmaceuticals the complexed metal ion must be radioactive. Radioisotopes of the elements technetium, rhenium, indium, gallium, copper, yttrium, samarium and holmium are suitable. For use as X-ray contrast applications the complexed metal ion must be able to absorb adequate amounts of the X-rays. These metal ions are generally refered to as radioopaque. Suitable elements for use as the radioopaque metal ion include lead, bismuth, gadolinium, dysprosium, holmium and praseodymium.

Examples of preferred compounds for radiopharmaceuticals are 1-[3-[N-(2,3-dihydroxypropyl)-N-(carboxymethyl)-amino]propyl]-4,7-bis-(carboxymethyl)-1,4,7-triazacyclononane, indium(III) complex; 1-[2-(4-carboxymethyl-piperazino)ethyl]-4,7-bis-(carboxymethyl)-1,4,7-triazacyclononane, technetium(III) complex; 1-[2-[N-(2-hydroxyethyl)-N-(phosphonomethyl)-amino]ethyl]-4,7-bis(phosphonomethyl)-1,4,7-triazacyclononane, technetium(III) complex; 1-[$N^3,N^6$-bis-[(2 -hydroxyethyl]-$N^6$-[sulfonomethyl)]-3,6-diaza]hexyl-4,7,-bis-(sulfonomethyl)- 1,4,7-triazacyclononane, gallium(III) complex; and 1-[$N^3,N^6$-bis-[(2-hydroxyethyl)]-$N^6$-[N-sulfonomethyl)]-3, 6-diaza]hexyl-4,7,-bis-(sulfonomethyl)-1,4,7-triazacyclononane, indium(III) complex.

Examples of preferred compounds for x-ray contrast are 1-[3-[N-(2,3-dihydroxypropyl)-N-(carboxymethyl)-amino] propyl]-4,7-bis-(carboxymethyl)-1,4,7-triazacyclononane, bismuth(III) complex; 1-[2-(4-carboxymethyl-piperazino-)ethyl]-4,7-bis-(carboxymethyl)- 1,4,7-triazacyclononane, holmium(III) complex; 1-[2-[N-(2-hydroxyethyl)-N-(phosphonomethyl)-amino]ethyl]-4,7 -bis(phosphonomethyl)-1,4,7-triazacyclononane, lead(II) complex; 1-[2-[N-(2-hydroxyethyl)-N(phosphonomethyl)amino]ethyl]-4,7-bis(phosphonomethyl)-1,4,7-triazacyclononane, bismuth(III) complex; and 1-[$N^3,N^6$-bis-[(2-hydroxyethyl)]

-N⁶-[N-sulfonomethyl)]-3,6-diaza]hexyl](-4,7,-bis-(sulfonomethyl)-1,4,7-triazacyclononane, dysprosium(III) complex.

The compositions of the invention can be formulated into therapeutic or diagnostic compositions for enteral or parenteral administration. These compositions contain an effective amount of the paramagnetic ion complex along with conventional pharmaceutical carriers and excipients appropriate for the type of administration contemplated. For example, parenteral formulations advantageously contain a sterile aqueous solution or suspension of from about 0.05 to about 1.0M of a paramagnetic ion complex according to this invention. Parenteral compositions may be injected directly or mixed with a large volume parenteral composition for systemic administration. Preferred parenteral formulations have a concentration of paramagnetic ion complex of about 0.1M to about 0.5M. Such solutions also may contain pharmaceutically acceptable buffers and, optionally, electrolytes such as sodium chloride. The compositions may advantageously contain a slight excess (e.g., from about 0.01 to about 15.0 mole % excess) of a complexing agent or its complex with a physiologically acceptable, non-toxic cation. Such physiologically acceptable, non-toxic cations include calcium ions, magnesium ions, copper ions, zinc ions, salts of n-methylglucamine and diethanolamine, and the like. Generally, calcium ions are preferred.

Formulations for enteral administration may vary widely, as is well-known in the art. In general, such formulations are liquids which include an effective amount of the paramagnetic ion complex in aqueous solution or suspension. Such enteral compositions may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired enhancement of the image. Such doses may vary widely, depending upon the particular paramagnetic ion complex employed, the organs or tissues which are the subject of the imaging procedure, the imaging procedure, the imaging equipment being used, and the like. In general, parenteral dosages will range from about 0.001 to about 1.0 mMol of paramagnetic ion complex per kg of patient body weight. Preferred parenteral dosages range from about 0.01 to about 0.5 mMol of paramagnetic ion complex per kg of patient body weight. Enteral dosages generally range from about 0.5 to about 100 mMol, preferably from about 1.0 to about 10 mMol, preferably from about 1.0 to about 20.0 mMol of paramagnetic ion complex per kg of patient body weight.

The diagnostic compositions of the invention are used in the conventional manner. The compositions may be administered to a patient, typically a warm-blooded animal, either systemically or locally to the organ or tissue to be imaged, and the patient then subjected to the imaging procedure. Protocols for imaging and instrument procedures are found in texts such as Stark, D. D.; Bradley, W. G. =i Magnetic Resonance Imaging; Mosby Year Book: St. Louis, Mo., 1992.

Radiopharmaceutical Imaging Procedures are found in Fred A. Mettler, Jr., M.D., M.P.H., Milton J. Guiberteau, M.D., *Essentials of Nuclear Medicine Imaging*, Grune and Stratton, Inc., New York, N.Y. 1983) and E. Edmund Kim, M.S., M.D. and Thomas P. Haynie, M.D., (MacMillan Publishing Co. Inc., New York, N.Y. 1987).

X-ray contrast Imaging Procedures are found in Albert A. Moss, M.D., Gordon Gamsu, M.D., and Harry K. Genant, M.D., *Computed Tomography of the Body*, (W. B. Saunders Company, Philadelphia, Pa. 1992) and M. Sovak, Editor, *Radiocontrast Agents*, (Springer-Verlag, Berlin 1984).

The following examples illustrate the specific embodiments of the invention described in this document. As would be apparent to skilled artisans, various changes and modifications are possible and are contemplated within the scope of the invention described.

EXAMPLES

Example 1

Synthesis of 1-[3-[N-(2,3-dihydroxypropyl)-N-(carboxymethyl)amino]propyl]-4,7-bis-(carboxymethyl)-1,4,7-triazacyclononane.

A mixture of ethylenediamine (18.0 g, 0.30 mol) and sodium carbonate (64.0 g, 0.60 mol) in 750 mL of deionized water was heated to 75 C. To the mixture was added p-toluenesulfonyl chloride (125.0 g, 0.66 mol) in 5 g portions over 45 min. Then the reaction was stirred at 75 C. for 15 hours. After the mixture was cooled to 25 C., the white precipitate was filtered, washed with water and dried in a vacuum desiccator at 1 mm to yield 1,4-bis(p-toluenesulfonyl)-1,4-diazabutane (100.1 g, 0.29 mol, 98%).

A solution of diethanolamine (30.0 g, 0.29 mol) in 300 mL of pyridine was cooled to 10 C. and methanesulfonyl chloride (108.6 g, 73.4 mL, 0.95 mol) was added dropwise. The mixture was then allowed to reach 25 C. and was stirred for 15 hours. The reaction was cooled to 0 C. and 1 L of cold 17% hydrochloric acid was added. The resulting brown precipitate was filtered and washed with water until the pH of the filtrate was neutral. The solid was recrystallized from 1:1 methanol/acetone solution to give 1,5-bis-(methanesulfonato)-3-methanesulfonyl-3-azapentane (22.0 g, 0.06 mol, 25%).

A slurry of 1,4-bis-(p-toluenesulfonyl)-1,4-diazabutane (10.0 g, 0.03 mol) and potassium carbonate (8.5 g, 0.06 mol) in 100 mL of anhydrous N,N-dimethylformamide was heated to 35 C. Then a solution of 1,5-bis-(methanesulfonato)-3 -methanesulfonyl-3-azapentane (9.5 g, 0.03 mol) in 100 mL of anhydrous N,N-dimethylformamide was added dropwise over 3 hours. The mixture was stirred at 35 C. for 4 days. The solvents were removed under reduced pressure and 250 g of ice was added to the residue with vigorous shaking. The crude solid was filtered and washed well with water. This material was refluxed in 200 mL of absolute ethanol for 15 hours and the resulting solid was filtered to give 1,4-bis-(p-toluenesulfonyl)- 7-methanesulfonyl-1,4,7-triazacyclononane (12.0 g, 0.02 mol, 76%).

A mixture of 1,4-bis-(p-toluenesulfonyl)-7-methanesulfonyl-1,4,7-triazacyclononane (38.8 g, 0.08 mol), 800 mL of glacial acetic acid and 150 mL of 48% hydrobromic acid was refluxed for 72 hours. The reaction solution was cooled to 25 C. and most of the solvents were removed under reduced pressure. Then 50 mL of 48% hydrobromic acid was added and the solvents were again evaporated. This procedure was repeated two more times to remove acetic acid. A mixture of 100 mL of absolute ethanol and 200 mL of diethyl ether was added and the solids were filtered. The solids were combined with sodium hydroxide pellets (18.0 g, 0.45 mol) in 250 mL of toluene and the mixture was refluxed for 15 hrs. The remaining solid was filtered and washed with 75 mL of hot toluene. The filtrate was concentrated to a volume of 60 mL and allowed to cool slowly to 25 C. The colorless crystals were filtered and dried to give 1-methanesulfonyl-1,4,7-triazacyclononane (11.1 g, 0.05 mol, 71%).

A solution of 1-methanesulfonyl-1,4,7-triazacyclononane (11.1 g, 0.05 mol) in 100 mL of deionized water is adjusted to pH 10 with 1N sodium hydroxide. Then bromoacetic acid (20.9 g, 0.15 mol) is added and the mixture is heated at 50 C. for 15 hours, keeping the pH at 10 by adding 1N sodium hydroxide as needed. The water is removed under reduced pressure to give 1,4-bis-(carboxymethyl)- 7-methanesulfonyl-1,4,7-triazacyclononane.

A mixture of 1,4-bis-(carboxymethyl)-7-methanesulfonyl-1,4,7-triazacyclononane (15.0 g, 0.05 mol) in 15 mL of concentrated sulfuric acid is stirred at 25 C. for 24 hours. The reaction mixture is cooled in an ice bath and 50 mL of water is slowly added. Then the pH of the solution is adjusted to 7 and the solvent is evaporated under reduced pressure. The residue is triturated with methanol several times and the combined methanol solutions are evaporated to give 1,4-bis-(carboxymethyl)- 1,4,7-triazacyclononane.

A solution of 2,2-dimethyl-4-aminomethyl-1,3-dioxolane (10.0 g, 0.08 mol) and triethylamine (8.1 g, 11.1 mL, 0.08 mol) in 100 mL of N,N-dimethylformamide is cooled to 0 C. under argon atmosphere. Then β-trimethylsilylethanesulfonyl chloride (16.0 g, 0.08 mol) is added dropwise. The solution is allowed to reach 25 C. and is stirred for 15 hours. The solvents are removed under reduced pressure and the crude residue is partitioned between dichloromethane (100 mL) and 5% sodium bicarbonate solution (50 mL). The layers are separated and the organic layer is dried over anhydrous sodium sulfate and evaporated to give 2,2-dimethyl-4-[N-(β-trimethylsilylethanesulfonyl)-aminomethyl]-1,3-dioxolane.

A mixture of 2,2-dimethyl-4-[N-β-trimethylsilylethanesulfonyl)aminomethyl]-1,3-dioxolane (20.7 g, 0.07 mol), 1-tosyloxy-3-benzyloxypropane (22.4 g, 0.07 mol), and potassium carbonate (9.7 g, 0.07 mol) in 250 mL of N,N-dimethylformamide is heated at 50 C. for 15 hours, under argon atmosphere. The solvent is removed under reduced pressure and the residue is partitioned between dichloromethane (200 mL) and water (100 mL). The layers are separated and the organic solution is dried over anhydrous sodium sulfate and evaporated to give 2,2-dimethyl-4-[N-(3-benzyloxypropyl)-N-(β-trimethylsilylethanesulfonyl)aminomethyl]-1,3-dioxolane.

A slurry of 2,2-dimethyl-4-[N-(3-benzyloxypropyl)-N-(β-trimethylsilylethanesulfonyl)aminomethyl]-1,3-dioxolane (26.6 g, 0.06 mol) and palladium hydroxide on carbon, Pd content 20% (5.0 g) in 100 mL of methyl alcohol is hydrogenated at 50 psi in a Parr apparatus for 4 hrs. The catalyst is removed by filtration through Celite and the filtrate is evaporated under reduced pressure to give 2,2-dimethyl-4-[N-(3-hydroxypropyl)-N-β-trimethyl-silylethanesulfonyl)aminomethyl]-1,3-dioxolane. The crude oil is dissolved in 75 mL of anhydrous pyridine and the solution is cooled to −10 C. Then portions of p-toluenesulfonyl chloride (11.4 g, 0.06 mol) are added over 1 hour. The resulting slurry is kept at −10 C. for 15 hours. Dichloromethane is added to the reaction mixture and the solution is washed two times with 10% hydrochloric acid (1 L total). The organic layer is dried over anhydrous sodium sulfate and evaporated to give 2,2-dimethyl-4-[N-(3 -tosyloxypropyl)-N-(β-trimethylsilylethanesulfonyl)aminomethyl]-1,3-dioxolane.

A slurry of 2,2-dimethyl-4-[N-(tosyloxypropyl)-N-(β-trimethylsilylethanesulfonyl)aminomethyl]-1,3 -dioxolane (25.4 g, 0.05 mol), 1,4-bis-(carboxymethyl)-1,4,7-triazacyclononane (12.3 g, 0.05 mol) and anhydrous potassium carbonate (6.9 g, 0.05 mol) in 200 mL of N,N-dimethylformamide is heated at 50 C. for 15 hours. The solvent is removed under reduced pressure and the residue is partitioned between dichloromethane (200 mL) and water (100 mL) The layers are separated and the organic layer is dried over anhydrous sodium sulfate and evaporated to give 1-{3-[2,2-dimethyl-4-N-(β-dimethyl-4-N-(β-trimethylsilylethanesulfonyl)aminomethyl-1,3-dioxolanyl]propyl}-4, 7-bis-(carboxymethyl)-1,4,7-triazacyclononane. The crude gum is then heated at 95 C. with cesium fluoride (22.8 g, 0.15 mol) in 200 mL of N,N' dimethylformamide. The solvent is evaporated under reduced pressure and the oil is dissolved in water and passed through reversed phase packing using a water/methanol gradient. The pure fractions are combined and evaporated to give 1-{3-[2,2-dimethyl-4-aminomethyl-1,3-dioxolanyl]-propyl}-4,7-bis-(carboxymethyl)-1,4,7-triazacyclononane.

A solution of 1-{3-[2,2-dimethyl-4-aminomethyl-1,3-dioxolanyl]-propyl}-4,7-bis-(carboxymethyl)-1,4,7-triazacyclononane (12.4 g, 0.03 mol) in 100 mL of deionized water is adjusted to pH 10 with 1N sodium hydroxide. Then bromoacetic acid (4.2 g, 0.03 mol) is added and the mixture is heated to 50 C. for 15 hours, keeping the pH of the solution between 9 and 10. Then the pH is adjusted to 4 with 1N hydrochloric acid and the solvent is evaporated under reduced pressure to give 1-[3-[N-(2,3-dihydroxypropyl)-N-(carboxymethyl)-amino]propyl]-4,7-bis-(carboxymethyl)-1, 4,7-triazacyclononane.

Example 2

Synthesis of 1-[3-[N-2,3-dihydroxypropyl)-N-(carboxymethyl)amino]propyl]-4,7-bis-(carboxymethyl)-1,4,7-triazacyclononane, gadolinium(III) complex.

To a solution of 1-[3-[N-(2,3-dihydroxypropyl)-N-(carboxymethyl)amino]propyl]4,7-bis(carboxymethyl)-1,4,7-triazacyclononane (5.0 g, 0.010 mol) in 50 mL of deionized water is added gadolinium oxide (1.8 g, 0.005 mol). The slurry is heated at 80 C. under argon atmosphere for 15 hours. The resulting solution is cooled at 25 C., filtered and the filtrate is evaporated under reduced pressure to give 1-[3-[N-2,3-dihydroxypropyl)-N-(carboxymethyl)amino]propyl]-4,7-bis-(carboxymethyl)- 1,4,7-triazacyclononane, gadolinium(III) complex.

Example 3

Synthesis of 1-[2-(4-carboxymethylpiperazino)ethyl]-4,7-bis-(carboxymethyl)- 1,4,7-triazacyclononane.

A mixture of ethylenediamine (18.0 g, 0.30 mol) and sodium carbonate (64.0 g, 0.60 mol) in 750 mL of deionized water was heated to 75 C. To the mixture was added p-toluenesulfonyl chloride (125.0 g, 0.66 mol) in 5 g portions over 45 minutes. Then the reaction was stirred at 75 C. for 15 hours. After the mixture was cooled to 25 C., the white precipitate was filtered, washed with water and dried in a vacuum desiccator at 1 mm to yield 1,4-bis(p-toluenesulfonyl)-1,4-diazabutane (100.1 g, 0.29 mol, 98%).

A solution of diethanolamine (30.0 g, 0.29 mol) in 300 mL of pyridine was cooled at 10 C. and methanesulfonyl chloride (108.6 g, 73.4 mL, 0.95 mol) was added dropwise. The mixture was then allowed to reach 25 C. and was stirred for 15 hours. The reaction was cooled to 0 C. and 1 L of cold 17% hydrochloric acid was added. The resulting brown precipitate was filtered and washed with water until the pH of the filtrate was nuetral. The solid was recrystallized from 1:1 methanol/acetone solution to give 1,5-bis-(methanesulfonato)-3-methanesulfonyl-3-azapentane (22.0 g, 0.06 mol, 25%).

A slurry of 1,4-bis-(p-toluenesulfonyl)-1,4-diazabutane (10.0 g. 0.03 mol) and potassium carbonate (8.5 g, 0.06 mol) in 100 mL of anhydrous N,N-dimethylformamide was heated to 35 C. Then a solution of 1,5-bis-(methanesulfonato)-3 methanesulfonyl-3-azapentane (9.5 g, 0.03 mol) in 100 mL of anhydrous N,N-dimethylformamide was added dropwise over 3 hours. The mixture was stirred at 35 C. for 4 days. The solvents were removed under reduced pressure and 250 g of ice was added to the residue with vigorous shaking. The crude solid was filtered and washed well with water. This material was refluxed in 200 mL of absolute ethanol for 15 hours and the resulting solid was filtered to give 1,4-bis-(p-toluenesulfonyl)- 7-methanesulfonyl-1,4,7-triazacyclononane (12.0 g, 0.02 mol, 76%).

A mixture of 1,4,-bis-(p-toluenesulfonyl)-7-methanesulfonyl-1,4,7-triazacyclononane (38.8 g, 0.08 mol) 800 mL of glacial acetic acid and 150 mL of 48% hydrobromic acid was refluxed for 72 hours. The reaction solution was cooled to 25 C. and most of the solvents were removed under reduced pressure. Then 50 mL of 48% hydrobromic acid were added and the solvents were again evaporated. This procedure was repeated two more times to remove acetic acid. A mixture of 100 mL of absolute ethanol and 200 mL of diethyl ether was added and the solids were filtered. The solids were combined with sodium hydroxide pellets (18.0 g, 0.45 mol) in 250 mL of toluene and the mixture was refluxed for 15 hours. The remaining solid was filtered and washed with 75 mL of hot toluene. The filtrate was concentrated to a volume of 60 mL and allowed to cool slowly to 25 C. The colorless crystals were filtered and dried to give 1-methanesulfonyl-1,4,7-triazacyclononane (11.1 g, 0.05 mol, 71%).

A solution of 1-methanesulfonyl-1,4,7-triazacyclononane (11.1 g, 0.05 mol) in 100 mL of deionized water is adjusted to pH 10 with 1N sodium hydroxide. Then bromoacetic acid (20.9 g, 0.15 mol) is added and the mixture is heated at 50 C. for 15 hours, keeping the pH at 10 by adding 1N sodium hydroxide as needed. The water is removed under reduced pressure to give 1,4-bis-(carboxymethyl)- 7-methanesulfonyl-1,4,7-triazacyclononane.

A mixture of 1,4-bis-(carboxymethyl)-7-methanesulfonyl-1,4,7-triazacyclononane (15.0 g, 0.05 mol) in 15 mL of concentrated sulfuric acid is stirred at 25 C. for 24 hours. The reaction mixture is cooled in an ice bath and 50 mL of water is slowly added. Then the pH of the solution is adjusted to 7 and the solvent is evaporated under reduced pressure. The residue is triturated with methanol several times and the combined methanol solutions are evaporated to give 1,4-bis-(carboxymethyl)- 1,4,7-triazacyclononane.

A mechanically-stirred solution of 1-(2-hydroxyethyl)piperazine (10.0 g, 9.4 mL, 0.07 mol) in 30 mL of deionized water is cooled to 0 C. Then portions of 4N sodium hydroxide (total 28 mL) and portions of benzyl chloroformate (18.8 g, 15.7 mL, 0.11 mol) are added over 15 minute periods, keeping the temperature at 0 C. to 5 C. At the end of the additions, 4N sodium hydroxide solution is added to bring the pH of the reaction mixture to 10. After 1 hour dichloromethane (200 mL) is added and the layers are separated. The organic solution is dried over anhydrous sodium sulfate and evaporated under reduced pressure to give 1-(2-hydroxyethyl)-4-carbobenzyloxypiperazine.

A solution of 1-(2-hydroxyethyl)-4-carbobenzyloxypiperazine (15.0 g, 0.06 mol) in 30 mL of anhydrous pyridine is cooled to 0 C. Then portions of p-toluenesulfonyl chloride (11.4 g, 0.06 mol) are added over 40 minutes. The slurry is kept at 0 C. for 15 hours. The mixture is dissolved in dichloromethane (100 mL) and washed with 10% hydrochloric acid (400 mL total), 10% sodium bicarbonate solution (100 mL) and saturated sodium chloride (100 mL). The organic solution is dried over anhydrous sodium sulfate and evaporated to give 1-(2-p-tosyloxyethyl)- 4-carbobenzyloxypiperazine.

A mixture of 1,4-bis-(carboxymethyl)-1,4,7-triazacyclononane (10.0 g, 0.04 mol), 1-(2-p-tosyloxyethyl)-4-carbobenzyloxypiperazine (16.7 g, 0.04 mol) and anhydrous potassium carbonate (5.5 g, 0.04 mol) in 100 mL of anhydrous N,N-dimethylacetmide is heated at 60 C. for 15 hours under argon atmosphere. The slurry is filtered after cooling to 25 C. and the solvent is removed under reduced pressure. The residue is partitioned between dichloromethane (200 mL) and water (100 mL). The layers are separated and the organic solution is dried over anhydrous sodium sulfate and evaporated to give 1-[2-(4-carbobenzyloxypiperazino)ethyl] -4,7-bis-(carboxymethyl)-1,4,7-triazacyclononane.

A slurry of 1-[2-(4-carbobenzyloxypiperazine)ethyl]-4,7-bis-(carboxymethyl)- 1,4,7-triazacyclononane (14.7 g, 0.03 mol) and 5% palladium on carbon (1.5 g) in 100 mL of methanol is hydrogenated at 50 psi using a Parr hydrogenation apparatus. After 8 hours, the catalyst is removed by filtration through Celite and the filtrate is evaporated under reduced pressure to give 1-(2-piperazinoethyl)-4,7-bis-(carboxymethyl)-1,4,7-triazacyclononane.

A solution of 1-(2-piperazinoethyl)-4,7-bis-(carboxymethyl)-1,4,7-triazacyclononane (10.7 g, 0.03 mol) in 100 mL of deionized water is adjusted to pH 10 with 1N sodium hydroxide solution. Then bromoacetic acid (4.2 g, 0.03 mol) is added and the solution is heated at 50 C. for 15 hours, keeping the pH between 9 and 10 with 1N sodium hydroxide. After cooling the reaction mixture to 25 C., the pH is adjusted to 4 with 1N hydrochloric acid. The solvent is removed under reduced pressure to give 1-[2-(4-carboxymethylpiperazino)ethyl]-4,7 -bis-(carboxymethyl)-1,4,7-triazacyclonane.

Example 4

Synthesis of 1-[2-(4-carboxymethylpiperazino)ethyl]-4,7-bis-(carboxymethyl)- 1,4,7-triazacyclononane, bismuth(III) complex.

Bismuth oxide (2.8 g, 0.006 mol) is added to a solution of 1-[2-(4-carboxymethylpiperazino)ethyl]-4,7-bis-(carboxymethyl)-1,4,7-triazacyclononane (5.0 g, 0.012 mol) in 50 mL of deionized water. The slurry is heated at 80 C. under argon atmosphere for 15 hours. The solution is cooled to 25 C., filtered and evaporated under reduced pressure to give 1-[2-(4-carboxymethylpiperazino)ethyl]-4,7-bis-(carboxymethyl)-1,4,7-triazacyclononane, bismuth(III) complex.

Although the invention has been described with respect to specific modifications, the details thereof are not to be construed as limitations, for it will be apparent that various equivalents, changes and modifications may be resorted to without departing from the spirit and scope thereof, and it is understood that such equivalent embodiments are to be included therein.

What is claimed is:

1. A compound of the formula:

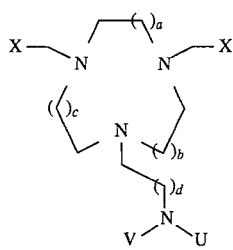

Wherein U is —$(CH_2)_nX$ or —$(CH_2)_nNR_1(CH_2)X$; $R_1$ is hydrogen, $C_1$–$C_8$ alkyl, $C_1$–$C_8$ hydroxyalkyl or $C_1$–$C_8$ alkoxyalkyl; V is —$(CH_2)_nX$—, —$(CH_2)_nNR_1(CH_2)X$, hydrogen, $C_1$–$C_8$ alkyl, $C_1$–$C_8$ hydroxyalkyl or $C_1$–$C_8$ alkoxyalkyl; V and $R_1$ may jointly be —$(CH_2)_m$— to form a heterocyclic ring; X is —$CO_2H$, —$PO_3H_2$, —$SO_3H$ or —$CONHOH$; a, b, c, d, n and m may be the same or different and are from one to about ten, preferably from one to about three.

2. The compound of claim 1 wherein U is —$(CH_2)_nX$; X is —$CO_2H$; V is —$CH_2CHOHCH_2OH$; a is 1, b is 1; c is 1; n is 1; and d is 2.

3. The compound of claim 1 wherein U is —$(CH_2)_n(NR_1)CH_2X$; X is —$CO_2H$; V is —$(CH_2)_m$—; $R_1$ is —$(CH_2)_m$—; a is 1; b is 1; c is 1; d is 1; m is 2; and n is 2.

4. The compound of claim 1 wherein U is —$(CH_2)_nX$; X is —$PO_3H_2$; V is —$CH_2CH_2OH$; a is 1; b is 1; c is 1; d is 1; and n is 1.

5. The compound of claim 1 wherein U is —$(CH_2)_n(NR_1)CH_2X$; X is —$SO_3H$; V is —$CH_2CH_2OH$; $R_1$ is —$CH_2CH_2OH$; a is 1; b is 1; c is 1; d is 1; and n is 2.

6. A compound of the formula:

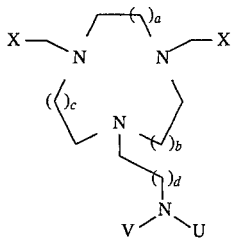

Wherein U is —$(CH_2)_nY$ or —$(CH_2)_nNR_1(CH_2)Y$; $R_1$ is hydrogen, $C_1$–$C_8$ alkyl, $C_1$–$C_8$ hydroxyalkyl or $C_1$–$C_8$ alkoxyalkyl; V is —$(CH_2)_nY$ or —$(CH_2)_nNR_1(CH_2)Y$, hydrogen, $C_1$–$C_8$ alkyl, $C_1$–$C_8$ hydroxyalkyl or $C_1$–$C_8$ alkoxyalkyl; optionally V and $R_1$ may jointly be —$(CH_2)_m$— to form a heterocyclic ring; Y is —$CO_2M$, —$PO_3HM$, —$SO_3M$ or —$CONHOM$; a, b, c, d, n and m may be the same or different and are from one to about ten, preferably from one to about three; M is a metal ion equivalent and/or a physiologically acceptable cation of an organic base.

7. The compound of claim 6 wherein U is —$(CH_2)_nY$; Y is $CO_2M$; V is $CH_2CHOHCH_2OH$; a is 1; b is 1; c is 1; n is 1; d is 2; and M is gadolinium.

8. The compound of claim 6 wherein U is —$(CH_2)_n(NR_1)CH_2Y$; Y is —$CO_2M$; V is —$(CH_2)_m$—; $R_1$ is —$(CH_2)_m$—; a is 1; b is 1; c is 1; d is 1; m is 2; n is 2; and M is gadolinium.

9. The compound of claim 6 wherein U is —$(CH_2)_nY$; Y is $PO_3HM$; V is $CH_2CH_2OH$; a is 1; b is 1; c is 1; d is 1; n is 1; and M is iron.

10. The compound of claim 6 wherein U is —$(CH_2)_nY$; Y is $PO_3HM$; V is $CH_2CH_2OH$; a is 1; b is 1; c is 1; d is 1; n is 1; and M is gadolinium.

11. The compound of claim 6 wherein U is —$(CH_2)_n(NR_1)CH_2Y$; Y is $SO_3M$; V is $CH_2CH_2OH$; $R_1$ is $CH_2CH_2OH$; a is 1; b is 1; c is 1; d is 1; n is 2; and M is gadolinium.

12. The compound of claim 6 wherein U is —$(CH_2)_nY$; Y is $CO_2M$; V is $CH_2CHOHCH_2OH$; a is 1; b is 1; c is 1; n is 1; d is 2; and M is bismuth.

13. The compound of claim 6 wherein U is —$(CH_2)_n(NR_1)CH_2Y$; Y is $CO_2M$; V is —$(CH_2)_m$—; $R_1$ is —$(CH_2)_m$—; a is 1; b is 1; c is 1; d is 1; m is 2; n is 2; and M is holmium.

14. The compound of claim 6 wherein U is —$(CH_2)_nY$; Y is —$PO_3HM$; V is —$CH_2CH_2OH$; a is 1; b is 1; c is 1; d is 1; n is 1; and M is lead.

15. The compound of claim 6 wherein U is —$(CH_2)_nY$; Y is $PO_3HM$; V is —$CH_2CH_2OH$; a is 1; b is 1; c is 1; d is 1; n is 1; and M is bismuth.

16. The compound of claim 6 wherein U is —$(CH_2)_n(NR_1)CH_2Y$; Y is $SO_3M$; V is —$CH_2CH_2OH$; $R_1$ is —$CH_2CH_2OH$; a is 1; b is 1; c is 1; d is 1; n is 2; and M is dysprosium.

17. The compound of claim 6 wherein U is —$(CH_2)_nY$; Y is —$CO_2M$; V is —$CH_2CHOHCH_2OH$; a is 1; b is 1; c is 1; n is 1; d is 2; and M is indium.

18. The compound of claim 6 wherein U is —$(CH_2)_n(NR_1)CH_2Y$; Y is —$CO_2M$; V is —$(CH_2)_m$—; $R_1$ is —$(CH_2)_m$—; a is 1; b is 1; c is 1; d is 1; m is 2; n is 2; and M is technetium.

19. The compound of claim 6 wherein U is —$(CH_2)_nY$; Y is —$PO_3HM$; V is —$CH_2CH_2OH$; a is 1; b is 1; c is 1; d is 1; n is 1; and M is technetium.

20. The compound of claim 6 wherein U is —$(CH_2)_n(NR_1)CH_2Y$; Y is $SO_3M$; V is —$CH_2CH_2OH$; $R_1$ is —$CH_2CH_2OH$; a is 1; b is 1; c is 1; d is 1; n is 2; and M is gallium.

21. The compound of claim 6 wherein U is —$(CH_2)_n(NR_1)CH_2Y$; Y is —$SO_3M$; V is —$CH_2CH_2OH$; $R_1$ is —$CH_2CH_2OH$; a is 1; b is 1; c is 1; d is 1; n is 2; and M is indium.

* * * * *